US012592322B2

(12) United States Patent
Bichey et al.

(10) Patent No.: US 12,592,322 B2
(45) Date of Patent: Mar. 31, 2026

(54) MULTI-MODAL DIGITAL COMMUNICATION ARCHITECTURE FOR PATIENT ENGAGEMENT

(71) Applicant: Nemedic, Inc., Westfield, IN (US)

(72) Inventors: Bradford G. Bichey, Westfield, IN (US); Andrew Richard Bichey, II, Denver, CO (US); Juan Vicente Rangel, Jr., Farmers Branch, TX (US)

(73) Assignee: Nemedic, Inc., Westfield, IN (US)

( * ) Notice: Subject to any disclaimer, the term of this patent is extended or adjusted under 35 U.S.C. 154(b) by 164 days.

(21) Appl. No.: 18/352,021

(22) Filed: Jul. 13, 2023

(65) Prior Publication Data

US 2025/0022617 A1    Jan. 16, 2025

(51) Int. Cl.
*G16H 80/00* (2018.01)
*G16H 10/60* (2018.01)
*H04L 65/1073* (2022.01)

(52) U.S. Cl.
CPC ............. *G16H 80/00* (2018.01); *G16H 10/60* (2018.01); *H04L 65/1073* (2013.01)

(58) Field of Classification Search
CPC ............................ G16H 80/00; H04L 65/1073
USPC ............................................................. 705/2
See application file for complete search history.

(56) References Cited

U.S. PATENT DOCUMENTS

2014/0050307 A1* 2/2014 Yuzefovich ........... H04M 15/41
                                                                   379/93.01
2019/0214116 A1* 7/2019 Eberting ................ G16H 40/20
2019/0294720 A1* 9/2019 Beringer ................ G06F 16/26
2019/0297069 A1* 9/2019 Miller ..................... H04W 4/14

OTHER PUBLICATIONS

H K Salinda Premadasa; Two-way text messaging: an interactive mobile learning environment in higher education; Research in Learning Technology 24 Association for Learning Technology. (2016) (Year: 2016).*
Gartner Glossary of Terms—Qualified Lead.
(Continued)

*Primary Examiner* — Hiep V Nguyen
(74) *Attorney, Agent, or Firm* — Taft Stettinius & Hollister LLP

(57) ABSTRACT
A method of leveraging a multi-modal digital communication architecture for patient engagement according to one embodiment includes generating a session identifier for a session between the computing system and a client device of a user in response to loading a web resource on the client device, creating a user journey in a database of the computing system, associating the session identifier with the user journey, validating user registration information of the user, wherein the user registration information includes a name of the user and a mobile number of a user mobile device of the user, receiving a user message from the user via the client device, and sending a Short Message Service (SMS) message to the user mobile device in response to receiving the user message from the user via the client device to establish an SMS-based communication channel with the user.

20 Claims, 5 Drawing Sheets

(56) References Cited

OTHER PUBLICATIONS

Committee on Optimizing Scheduling in Health Care; Institute of Medicine; Kaplan G, Lopez MH, McGinnis JM, editors. Transforming Health Care Scheduling and Access: Getting to Now. Washington (DC): National Academies Press (US); Aug. 24, 2015. Available from: https://www.ncbi.nlm.nih.gov/books/NBK316132/ doi: 10.17226/20220.

Sanborn, Hospitals are losing money on employed physicians: Here's how to save the bottom line and your staff, https://www.healthcarefinancenews.com/news/hospitals-are-losing-money-employed-physicians-heres-how-save-bottom-line-and-your-staff, May 31, 2018.

Latest PAI Research Efforts, Physicians Advocacy Institute, http://www.physiciansadvocacyinstitute.org/PAI-Research/Physician-Employment-and-Practice-Acquisitions-Trends-2019-21.

Hampton, Cancer, cardiac, urology, orthopedic—both urgent and elective—among the backlogs, https://news.harvard.edu/gazette/story/2022/08/surgical-procedures-havent-recovered-from-covid/#:~: text=Reductions%20in%20many%20types%20of,MassachU.Setts%20General%20Hospital%20has%20found, Aug. 23, 2022.

Coronavirus: impact on online usage in the U.S.—Statistics & Facts, https://www.statista.com/topics/6241/coronavirus-impact-on-online-usage-in-the-US/#topicOverview.

Plott et al., Unexpected Health Insurance Profits and the COVID-19 Crisis. JAMA. 2020;324(17):1713-1714. doi:10.1001/jama.2020.19925.

Violation Tracker Current Parent Company Summary, https://violationtracker.goodjobsfirst.org/parent/unitedhealth-group.

King, House passes bill to install electronic prior authorization in Medicare Advantage plans, https://www.fiercehealthcare.com/payers/house-passes-bill-install-electronic-prior-authorization-medicare-advantage-plans, Sep. 14, 2022.

During uncertain times, one thing is certain—the AMA is fighting for you., https://www.ama-assn.org/amaone/ama-recovery-plan-america-s-physicians.

Mensik, Half of nurses consider leaving the profession, survey finds, https://www.healthcaredive.com/news/covid-pandemic-nurse-burnout-leaving-profession-connectRN/636033/#:~: text=Staffing%20shortages%20were%20the%20top,feel%20a%20lack%20of%20appreciation, Nov. 8, 2022.

Clemens et al., The Minimum Wage and the Great Recession: Evidence of Effects on the Employment and Income Trajectories of Low-Skilled Workers, NBER Working Paper Series, Dec. 2014.

Pethokoukis et al., https://www.aei.org/economics/how-does-raising-the-minimum-wage-affect-the-labor-market-my-long-read-qa-with-jeffrey-clemens/, May 17, 2021.

Dobson, Trauma of major surgery: A global problem that is not going away. Int J Surg. Sep. 2020;81:47-54. doi: 10.1016/j.ijsu.2020.07.017. Epub Jul. 29, 2020. PMID: 32738546; PMCID: PMC7388795.

Best et al., The likely economic impact of fewer elective surgical procedures on US hospitals during the COVID-19 pandemic. Surgery. Nov. 2020; 168(5):962-967. doi: 10.1016/j.surg.2020.07.014. Epub Jul. 29, 2020. PMID: 32861440; PMCID: PMC7388821.

Pant, The impact of interest rates on home ownership—a primer, https://www.opendoor.com/articles/impact-of-interest-rates-on-home-ownership, Mar. 30, 2018.

Wong et al., Development and Assessment of a Systematic Approach for Detecting Disparities in Surgical Access. JAMA Surg. Mar. 1, 2021;156(3):239-245. doi: 10.1001/jamasurg.2020.5668. PMID: 33326009; PMCID: PMC7745135.

Delay of needed care, https://www.healthsystemtracker.org/indicator/access-affordability/delay-needed-care/#Percent %20of%20adults%20who%20reported%20delaying%20or%20going%20without%20medical%20care%20due%20to%20COVID-19,%202021.

McGough et al., How has U.S. spending on healthcare changed over time?https://www.healthsystemtracker.org/chart-collection/u-s-spending-healthcare-changed-time/#Annual%20change%20in%20price%20and%20quantity%20indexes%20of%20health%20services,%201980-2020,%20index%20numbers%202012=100.

Durden, Something is Rigged: Unexplained, Record 2.7 Million Jobs Gap Emerges in Broken Payrolls Report, https://www.zerohedge.com/markets/something-rigged-unexplained-record-27-million-jobs-gap-emerges-broken-payrolls-report, Dec. 3, 2022.

Muoio, Physicians say COVID-19 has lowered their trust in organizational leadership and healthcare at large, https://www.fiercehealthcare.com/hospitals/physicians-say-covid-19-has-lowered-their-trust-organizational-leadership-and-healthcare, May 24, 2021.

Muoio, A 'pandemic of mistrust' is prolonging COVID-19 and undermining future care, AMA president says, https://www.fiercehealthcare.com/providers/pandemic-distrust-prolonging-covid-19-and-undermining-future-care-ama-president-says, Feb. 24, 2022.

Peck et al., Latin America Indicator Research Coalition examines prehospital care using a trauma systems application of LCoGS indicator 1, Jul. 2017, Bulletin of the American College of Surgeons 102(7):23-31.

Analysis: 88% of Large Health Systems are Losing Money in 2022, https://www.ascendient.com/higher-thinking/healthcare-financial-planning-88-of-large-health-systems-are-losing-money-in-2022.

* cited by examiner

300

WEB PAGE LOADED ON CLIENT DEVICE — 302

NEW SESSION CREATED — 304

306 — SESSION IDENTIFIER GENERATED

CREATE NEW USER JOURNEY IN DATABASE — 308

ASSOCIATE SESSION IDENTIFIER WITH
NEW USER JOURNEY — 310

PROMPT USER FOR USER
REGISTRATION INFORMATION — 312

RECEIVE USER REGISTRATION INFORMATION — 314

A   TO

MULTI-MODAL DIGITAL COMMUNICATION ARCHITECTURE FOR PATIENT ENGAGEMENT

BACKGROUND

Blocked surgical care of patients has become one of the greatest strains on the United States healthcare system. Although the United States has often been recognized as a leader in innovation for surgical procedures worldwide, the technical framework and infrastructure for patient engagement, qualification, and communication is lacking. Accordingly, the multi-modal digital communication architecture for patient engagement and underlying technologies described herein serve to close that technical gap.

SUMMARY

One embodiment is directed to a unique system, components, and methods for leveraging a multi-modal digital communication architecture for patient engagement. Other embodiments are directed to apparatuses, systems, devices, hardware, methods, and combinations thereof for leveraging a multi-modal digital communication architecture for patient engagement.

According to an embodiment, a method of leveraging a multi-modal digital communication architecture for patient engagement may include generating, by a computing system, a session identifier for a session between the computing system and a client device of a user in response to loading a web resource on the client device, creating, by the computing system, a user journey in a database of the computing system, associating, by the computing system, the session identifier with the user journey, validating, by the computing system, user registration information of the user, wherein the user registration information includes a name of the user and a mobile number of a user mobile device of the user, receiving, by the computing system, a user message from the user via the client device, and sending, by the computing system, a Short Message Service (SMS) message to the user mobile device in response to receiving the user message from the user via the client device to establish an SMS-based communication channel with the user.

In some embodiments, the user mobile device may be or include the client device.

In some embodiments, the method may further include associating the user journey with the user registration information.

In some embodiments, the method may further include storing the user message and the SMS message to the database in association with the user journey.

In some embodiments, validating the user registration information of the user may include transmitting, by the computing system, a random code to the user mobile device via SMS, and receiving, by the computing system, a user entry of the random code via the client device.

In some embodiments, the method may further include analyzing, by the computing system, the user journey using machine learning to prequalify the user for a particular procedure.

In some embodiments, analyzing the user journey may include analyzing one or more images of the user using computer vision.

In some embodiments, analyzing the user journey may include analyzing the user journey using machine learning based on patient data of the user and insurance criteria.

In some embodiments, analyzing the user journey may include analyzing at least one of diagnostic lab data for the user or electronic health record provider note information associated with a user visit.

In some embodiments, the method may further include generating a refined note based on the analysis of the user journey using machine learning to prequalify the user for the particular procedure.

According to another embodiment, a computing system for leveraging a multi-modal digital communication architecture for patient engagement may include at least one processor and at least one memory comprising a plurality of instructions stored thereon that, in response to execution by the at least one processor, causes the computing system to generate a session identifier for a session between the computing system and a client device of a user in response to loading a web resource on the client device, create a user journey in a database of the computing system, associate the session identifier with the user journey, validate user registration information of the user, wherein the user registration information includes a name of the user and a mobile number of a user mobile device of the user, receive a user message from the user via the client device, and send a Short Message Service (SMS) message to the user mobile device in response to receipt of the user message from the user via the client device to establish an SMS-based communication channel with the user.

In some embodiments, the user mobile device may be or include the client device.

In some embodiments, the plurality of instructions may further cause the computing system to associate the user journey with the user registration information.

In some embodiments, the plurality of instructions may further cause the computing system to store the user message and the SMS message to the database in association with the user journey.

In some embodiments, to validate the user registration information of the user may include to transmit a random code to the user mobile device via SMS, and receive a user entry of the random code via the client device.

In some embodiments, the plurality of instructions may further cause the computing system to analyze the user journey using machine learning to prequalify the user for a particular procedure.

In some embodiments, to analyze the user journey may include to analyze one or more images of the user using computer vision.

In some embodiments, to analyze the user journey may include to analyze the user journey using machine learning based on patient data of the user and insurance criteria.

In some embodiments, to analyze the user journey may include to analyze at least one of diagnostic lab data for the user or electronic health record provider note information associated with a user visit.

In some embodiments, the plurality of instructions may further cause the computing system to generate a refined note based on the analysis of the user journey using machine learning to prequalify the user for the particular procedure.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
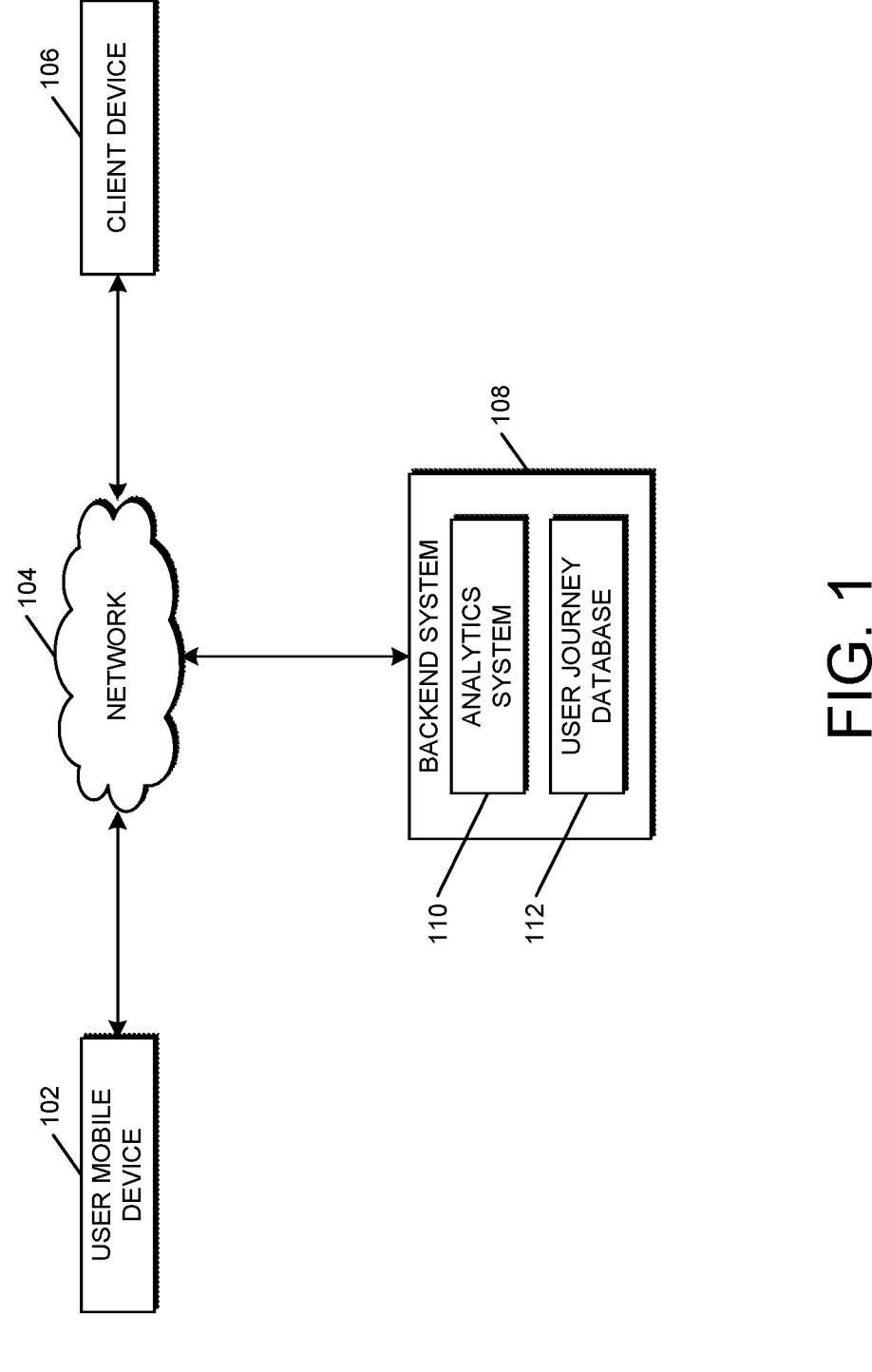
FIG. 1 is a simplified block diagram of at least one embodiment of a system for leveraging a multi-modal digital communication architecture for patient engagement.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

The terms longitudinal, lateral, and transverse may be used to denote motion or spacing along three mutually perpendicular axes, wherein each of the axes defines two opposite directions. The directions defined by each axis may also be referred to as positive and negative directions. Additionally, the descriptions that follow may refer to the directions defined by the axes with specific reference to the orientations illustrated in the figures. For example, the directions may be referred to as distal/proximal, left/right, and/or up/down. It should be appreciated that such terms may be used simply for ease and convenience of description and, therefore, used without limiting the orientation of the system with respect to the environment unless stated expressly to the contrary. For example, descriptions that reference a longitudinal direction may be equally applicable to a vertical direction, a horizontal direction, or an off-axis orientation with respect to the environment. Furthermore, motion or spacing along a direction defined by one of the axes need not preclude motion or spacing along a direction defined by another of the axes. For example, elements described as being "laterally offset" from one another may also be offset in the longitudinal and/or transverse directions, or may be aligned in the longitudinal and/or transverse directions. The terms are therefore not to be construed as further limiting the scope of the subject matter described herein.

Referring now to FIG. 1, the illustrative system 100 for leveraging a multi-modal digital communication architecture for patient engagement includes a user mobile device 102, a network 104, a client device 106, and a backend system 108. Additionally, the illustrative backend system 108 includes an analytics system 110 and a user journey database 112. It should be appreciated that the user mobile device 102, the network 104, the client device 106, the backend system 108, the analytics system 110, and the user journey database 112 may be embodied as any type of device or collective of devices suitable for performing the functions described herein. Additionally, although the user journey database 112 is described herein as a device or collection of devices in the illustrative embodiment, it should be appreciated that the user journey database 112 may be embodied as any suitable data structure(s) suitable for containing the user journey and/or other data described herein, and such user journey database 112 may be stored on one or more devices. Further, although the user journey database 112 is described herein in the singular, it should be appreciated that the user journey database 112 may be composed of multiple databases and/or data structures in other embodiments.

In the illustrative embodiment, the user mobile device 102 is embodied as a smartphone, cellular, or other type of mobile device capable of communicating Short Message Service (SMS) messages (also referred to as "text messages"), and accessible/usable by a user or patient. However, in other embodiments, it should be appreciated that the user mobile device 102 may be embodied as any other type of computing device capable of SMS-based communication such as, for example, a desktop computer, laptop computer, tablet computer, and/or other SMS-enabled communication device. In some embodiments, the user mobile device 102 may be configured to execute one or more applications for performing various functions described herein (e.g., when functioning as the client device 106). For example, in some embodiments, one or more of the applications may serve as a client-side user interface (e.g., via a web browser or local interface) for a web-based application or service (e.g., of the backend system 108 and/or another computing device).

The network 104 may be embodied as any type of communication network capable of facilitating communication between the various devices of the system 100. As such, the network 104 may include one or more networks, routers, switches, computers, and/or other intervening devices. For example, the network 104 may be embodied as or otherwise include one or more cellular networks, telephone networks, local or wide area networks, publicly available global networks (e.g., the Internet), ad hoc networks, short-range communication links, or a combination thereof.

In some embodiments, the client device 106 may be embodied as a desktop computer, laptop computer, tablet computer, smartphone, or other computing device configured to allow a user of the user mobile device 102 to interact with the backend system 110, web servers, and/or other computing devices of the system 100. For example, as described herein, the user may utilize the client device 106 to access a web page or other web resource to register as a patient with the backend system 108 and establish multimodal communication with a medical concierge. Although described herein as being an independent device, it should be appreciated that, in some embodiments, the client device 106 may be embodied as a sub-system of another device and/or application executed on another device (e.g., a web browser). For example, in some embodiments, the user may utilize the user mobile device 102 as the client device 106 in that the user mobile device 102 executes an application (e.g., a web browser) to launch a web page or web resource as described herein.

The backend system 108 may be embodied as any type of device(s) capable of performing the functions described herein. In the illustrative embodiment, the backend system 108 includes the analytics system 110 and the user journey database 112. It should be appreciated that the backend system 108 may include one or more servers and/or user interface devices (e.g., for use by a concierge or administrator). Although described primarily as a human concierge for brevity of the description, it should be appreciated that the concierge may be embodied as an automated concierge in some embodiments to perform one or more of the functions of the concierge described herein. In such embodiments, the automated concierge may be embodied as any automated service or system capable of using automation to engage with users and otherwise performing the functions described herein. For example, in some embodiments, the automated concierge may operate as an executable program that can be launched according to the demand for the particular automated concierge (e.g., by the backend system 108). In various embodiments, the automated concierge may simulate and process human conversation (e.g., either written or spoken), allowing human users to interact with digital devices as if the humans were communicating with another human. Accordingly, in some embodiments, the automated concierge may leverage speech-to-text (STT) and/or text-to-speech (TTS) techniques to facilitate communication with users depending on the particular medium of communication (e.g., via SMS). In some embodiments, the automated concierge includes and/or leverages artificial intelligence, adaptive learning, bots, cognitive computing, and/or other automation technologies.

As described in greater detail below, the analytics system 110 may be configured to analyze various data stored to the user journey database 112 using machine learning, computer vision, and/or other analytical technologies. For example, the backend system 108 or, more specifically, the analytics system 110 may execute various computer vision algorithms, filters, and/or techniques to generate processed versions of images and/or reformatted versions thereof (e.g., to further analyze medical imaging for patient prequalification purposes). In particular, in some embodiments, the backend system 108 may utilize image filters (e.g., kernel-based convolution, masking, etc.), edge detection algorithms (e.g., Canny edge detection, Sobel filters, etc.), image segmentation algorithms (e.g., pyramid segmentation, watershed segmentation, etc.), blob detection algorithms, corner detection algorithms, features identification and/or matching algorithms (e.g., scale-invariant feature transform (SIFT), speeded-up robust features (SURF), etc.), morphological image processing algorithms (e.g., erosion, dilation, opening, closing, etc.), and/or other suitable algorithms useful in performing the functions described herein.

Further, in some embodiments, the backend system 108 or, more specifically, the analytics system 110 may leverage machine learning to improve the prequalification of a patient, refine a note, and/or for other relevant purposes as described herein. For example, in some embodiments, the backend system 108 may utilize neural network algorithms, regression algorithms, instance-based algorithms, regularization algorithms, decision tree algorithms, Bayesian algorithms, clustering algorithms, association rule learning algorithms, deep learning algorithms, dimensionality reduction algorithms, and/or other suitable machine learning algorithms, techniques, and/or mechanisms. It should be further appreciated that the backend system 108 may leverage one or more artificial intelligence models for natural language processing and/or other processing including, for example, large language models.

It should be appreciated that, in some embodiments, one or more servers of the backend system 108 may be embodied as a cloud-based device or collection of devices within a cloud computing environment. Further, in cloud-based embodiments, such servers may be embodied as a server-ambiguous computing solution, for example, that executes a plurality of instructions on-demand, contains logic to execute instructions only when prompted by a particular activity/trigger, and does not consume computing resources when not in use. That is, the server(s) may be embodied as a virtual computing environment residing "on" a computing system (e.g., a distributed network of devices) in which various virtual functions (e.g., Lambda functions, Azure functions, Google cloud functions, and/or other suitable virtual functions) may be executed corresponding with the functions of the server(s) described herein. For example, when an event occurs (e.g., data is transferred to the server(s) for handling), the virtual computing environment may be communicated with (e.g., via a request to an API of the virtual computing environment), whereby the API may route the request to the correct virtual function (e.g., a particular server-ambiguous computing resource) based on a set of rules. As such, when a request for the transmission of access control data is made (e.g., via an appropriate user interface to the server(s)), the appropriate virtual function(s) may be executed to perform the actions before eliminating the instance of the virtual function(s).

It should be appreciated that each of the user mobile device 102, the client device 106, the backend system 108, and/or the analytics system 110 may be embodied as a computing device/system similar to the computing system 200 described below in reference to FIG. 2. For example, in the illustrative embodiment, one or more of the user mobile device 102, the client device 106, the backend system 108, and/or the analytics system 110 may include a processing device 202 and a memory 206 having stored thereon operating logic 208 for execution by the processing device 202 for operation of the corresponding device.

Figure 2:
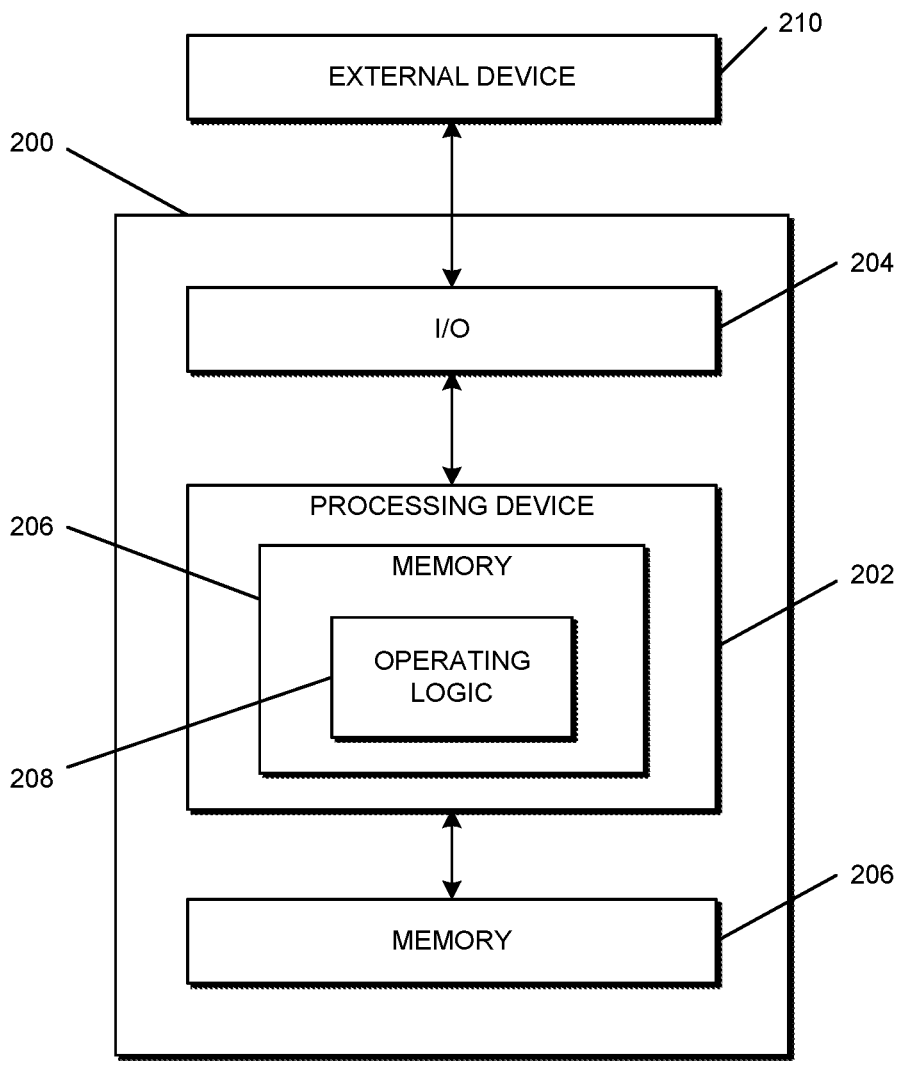
FIG. 2 is a simplified block diagram of at least one embodiment of a computing system.

Referring now to FIG. 2, a simplified block diagram of at least one embodiment of a computing system 200 is shown. The illustrative computing system 200 depicts at least one embodiment of the user mobile device 102, the client device 106, the backend system 108, and/or the analytics system 110 illustrated in FIG. 1. Depending on the particular embodiment, the computing system 200 may be embodied as a mobile computing device, server, desktop computer, laptop computer, tablet computer, notebook, netbook, Ultrabook™, cellular phone, smartphone, wearable computing device, personal digital assistant, Internet of Things (IoT) device, control panel, router, gateway, and/or any other computing, processing, and/or communication device capable of performing the functions described herein.

The computing system 200 includes a processing device 202 that executes algorithms and/or processes data in accordance with operating logic 208, an input/output device 204 that enables communication between the computing system 200 and one or more external devices 210, and memory 206 which stores, for example, data received from the external device 210 via the input/output device 204.

The input/output device 204 allows the computing system 200 to communicate with the external device 210. For example, the input/output device 204 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry may be configured to use any one or more communication technologies (e.g., wireless or wired communications) and associated protocols (e.g., Ethernet, Bluetooth®, Wi-Fi®, WiMAX, etc.) to effect such communication depending on the particular computing system 200. The input/output device 204 may include hardware, software, and/or firmware suitable for performing the techniques described herein.

The external device 210 may be any type of device that allows data to be inputted or outputted from the computing system 200. For example, in various embodiments, the external device 210 may be embodied as the user mobile device 102, the client device 106, the backend system 108, or the analytics system 110. Further, in some embodiments, the external device 210 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 210 may be integrated into the computing system 200.

The processing device 202 may be embodied as any type of processor(s) capable of performing the functions described herein. In particular, the processing device 202 may be embodied as one or more single or multi-core processors, microcontrollers, or other processor or processing/controlling circuits. For example, in some embodiments, the processing device 202 may include or be embodied as an arithmetic logic unit (ALU), central processing unit (CPU), digital signal processor (DSP), and/or another suitable processor(s). The processing device 202 may be a programmable type, a dedicated hardwired state machine, or a combination thereof. Processing devices 202 with multiple processing units may utilize distributed, pipelined, and/or parallel processing in various embodiments. Further, the processing device 202 may be dedicated to performance of just the operations described herein, or may be utilized in one or more additional applications. In the illustrative embodiment, the processing device 202 is of a programmable variety that executes algorithms and/or processes data in accordance with operating logic 208 as defined by programming instructions (such as software or firmware) stored in memory 206. Additionally or alternatively, the operating logic 208 for processing device 202 may be at least partially defined by hardwired logic or other hardware. Further, the processing device 202 may include one or more components of any type suitable to process the signals received from input/output device 204 or from other components or devices and to provide desired output signals. Such components may include digital circuitry, analog circuitry, or a combination thereof.

The memory 206 may be of one or more types of non-transitory computer-readable media, such as a solid-state memory, electromagnetic memory, optical memory, or a combination thereof. Furthermore, the memory 206 may be volatile and/or nonvolatile and, in some embodiments, some or all of the memory 206 may be of a portable variety, such as a disk, tape, memory stick, cartridge, and/or other suitable portable memory. In operation, the memory 206 may store various data and software used during operation of the computing system 200 such as operating systems, applications, programs, libraries, and drivers. It should be appreciated that the memory 206 may store data that is manipulated by the operating logic 208 of processing device 202, such as, for example, data representative of signals received from and/or sent to the input/output device 204 in addition to or in lieu of storing programming instructions defining operating logic 208. As shown in FIG. 2, the memory 206 may be included with the processing device 202 and/or coupled to the processing device 202 depending on the particular embodiment. For example, in some embodiments, the processing device 202, the memory 206, and/or other components of the computing system 200 may form a portion of a system-on-a-chip (SoC) and be incorporated on a single integrated circuit chip.

In some embodiments, various components of the computing system 200 (e.g., the processing device 202 and the memory 206) may be communicatively coupled via an input/output subsystem, which may be embodied as circuitry and/or components to facilitate input/output operations with the processing device 202, the memory 206, and other components of the computing system 200. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing system 200 may include other or additional components, such as those commonly found in a typical computing device (e.g., various input/output devices and/or other components), in other embodiments. It should be further appreciated that one or more of the components of the computing system 200 described herein may be distributed across multiple computing devices. In other words, the techniques described herein may be employed by a computing system that includes one or more computing devices. Additionally, although only a single processing device 202, I/O device 204, and memory 206 are illustratively shown in FIG. 2, it should be appreciated that a particular computing system 200 may include multiple processing devices 202, I/O devices 204, and/or memories 206 in other embodiments. Further, in some embodiments, more than one external device 210 may be in communication with the computing system 200.

Figures 3, 4:
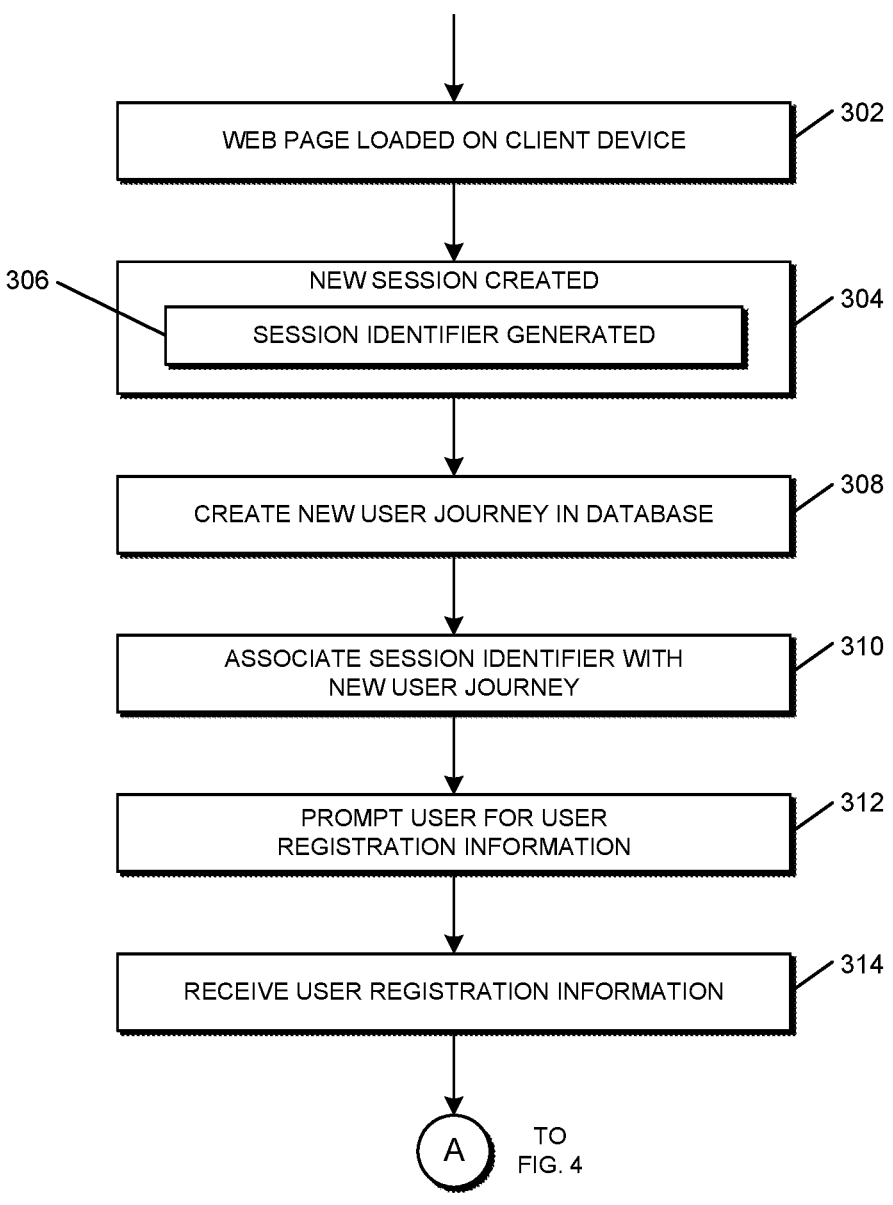
FIGS. 3-4 are a simplified flow diagram of at least one embodiment of a method for establishing multi-modal digital communication with a patient.
Figure 4:
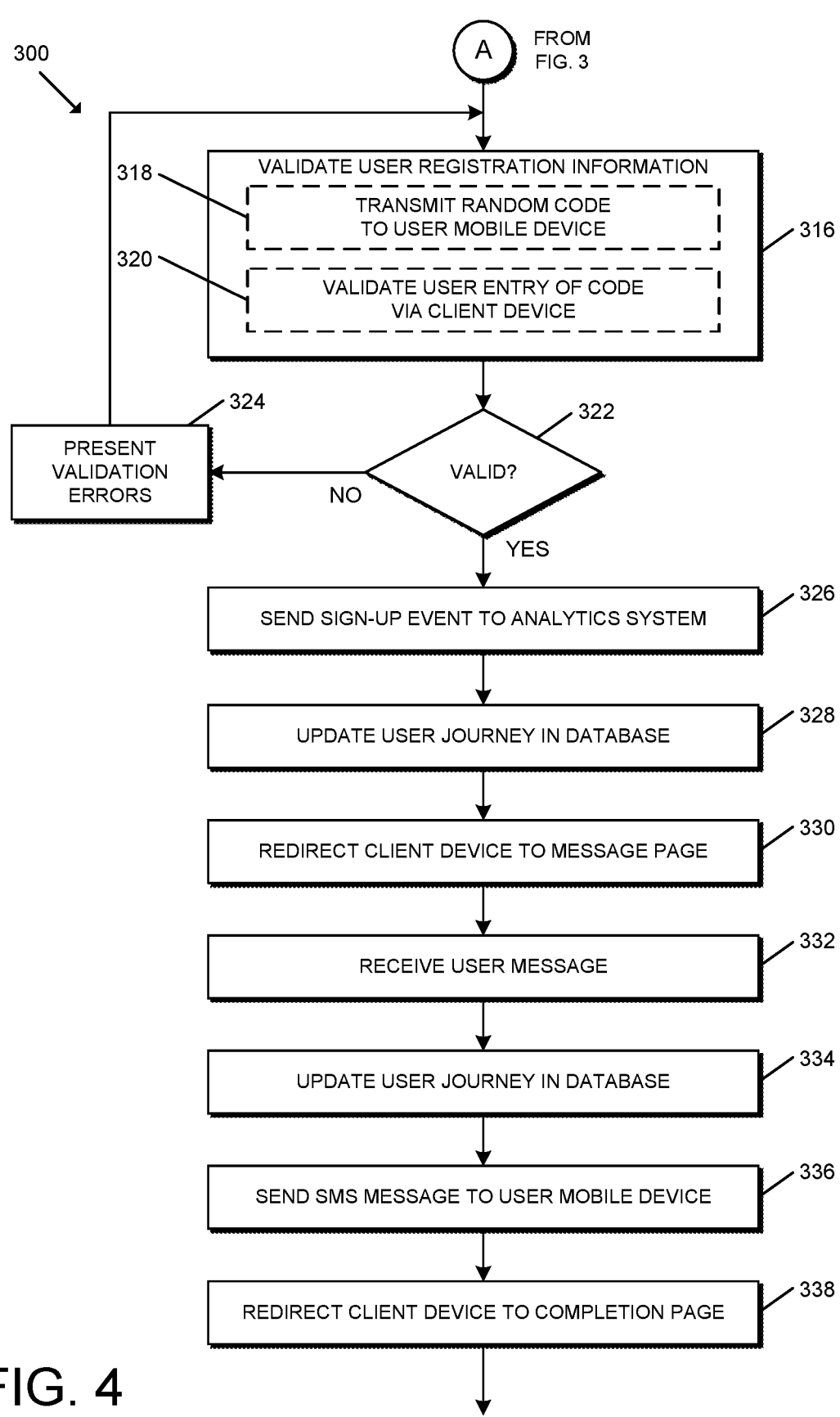

Referring now to FIGS. 3-4, in use, the system 100 may execute a method 300 for establishing multi-modal digital communication with a patient. It should be appreciated that the particular blocks of the method 300 are illustrated by way of example, and such blocks may be combined or divided, added or removed, and/or reordered in whole or in part depending on the particular embodiment, unless stated to the contrary.

The illustrative method 300 begins with block 302 of FIG. 3 in which the user loads a web page or other web resource on the client device 106. For example, in some embodiments, the user may use the client device 106 to access a web page associated with the backend system 108. In block 304, in response to loading the web page or other web resource, a new session is created for the client device 106. Accordingly, in block 306, the client device 106 and/or the web server generates a session identifier (or tracking identifier) for a session between the client device and the web server. In some embodiments, the session identifier may be generated using JavaScript; however, it should be appreciated that the session identifier may be otherwise generated in other embodiments.

In block 308, the backend system 108 creates a new user journey in the user journey database 112 and, in block 310, the backend system 108 associates the session identifier with the new user journey (e.g., storing the session identifier in the user journey database 112 in association with the new user journey). It should be appreciated that, in some embodiments, the analytics system 110 is able to access data stored in the user journey database 112 and, therefore, is able to analyze the relevant user journey data and changes made thereto (e.g., in real time and/or at a later time). In other embodiments, the updates made to the user journey database 112 may also be transmitted to the analytics system 110 for analysis. In the illustrative embodiment, as the user interacts with the web page or other web resource, events may be generated in association with that particular session identifier and, therefore, may be stored to the associated user journey in the user journey database 112 accordingly.

In block 312, the user is prompted by the web page or other web resource to provide various user registration information via the client device 106. For example, in some embodiments, the user is prompted to provide the user's name (e.g., first name and last name), phone number (e.g., of the user mobile device 102), user identifier, other bibliographic information, preliminary health disclosures, and/or other relevant user registration information. In block

314, the backend system 108 receives the user registration information provided by the user via the client device 106.

In block 316 of FIG. 4, the backend system 108 validates (or attempts to validate) the user registration information provided by the user via the client device 106. For example, the backend system 108 may ensure that each of the required information components is accurately provided (e.g., first name, last name, phone number, etc.). For example, the backend system 108 may validate that the first name and last name are provided in acceptable alphabetical characters (e.g., in the proper language alphabet, not including numbers or special characters, etc.). Additionally, the backend system 108 may validate that the provided phone number is a cellular/mobile phone number or another phone number capable of receiving SMS messages. The backend system 108 may also validate that the provided phone number is in fact associated with the user mobile device 102 of the user. To do so, in block 318, the backend system 108 may randomly generate a code (e.g., a 6-digit code) and transmit the random code to the user mobile device 102 via SMS. The user may then provide the random code to the backend system 108 via a prompt on the client device 106 and, in block 320, the backend system 108 may validate the user entry of the random code. If the user-entered code matches the random code generated by the backend system 108, then the phone number is validated. It should be appreciated, however, that the backend system 108 may otherwise validate the user's phone number in other embodiments. For example, in another embodiment, the backend system 108 may send an SMS message to the user mobile device 102 that includes a link that may be clicked by the user to generate a message to the backend system 108 that validates the phone number.

If the backend system 108 determines, in block 322, that one or more components of the user registration information is not valid, the method 300 advances to block 324 in which the client device 106 and/or the user mobile device 102 may present validation errors to the user. For example, the user may be prompted to supply the correct information, which may be re-validated. However, if the backend system 108 determines that the user registration information is valid, the method 300 advances to block 326 in which the backend system 108 may send a sign-up event to the analytics system 110 along with the associated information (e.g., the user registration information, session identifier, user identifier, and/or other relevant data). In some embodiments, it should be appreciated that one or more of the events generated may be generated based on a JavaScript handler. Additionally, in block 328, the backend system 108 may update the user journey in the user journey database 112 to include the user registration information. Further, in some embodiments, the user journey may be associated with a unique user identifier for the user, which may be generated or pre-existing in association with the user (e.g., based on first name, last name, and/or other unique identifying information) depending on the particular embodiment.

In block 330, the user is redirected to a message page that prompts the user to enter a message to the medical concierge. More specifically, the client device 106 may load a web page or other web resource that provides one or more text fields for the user to enter a message. For example, the user may enter a message such as "I need to see a doctor for my hip" via the client device 106. In block 332, the backend system 108 receives the user message, which may be provided to the medical concierge via a user interface of the backend system 108. In block 334, the backend system 108 updates the user journey in the user journey database 112 to include the user message and/or related information (e.g., time stamp, meta data, etc.).

In block 336, the backend system 108 sends an SMS message to the user mobile device 102 via the phone number provided with the user registration information (and therefore the phone number associated with the user journey). In the illustrative embodiment, the user is able to respond to the phone number through which the backend system 108 sends the SMS message. Accordingly, it should be appreciated that the transmission of the SMS message to the user mobile device 102 establishes an SMS-based communication channel with the user, thereby allowing the user to seamlessly and efficiently communicate with the medical concierge via a more convenient and familiar communication medium. In some embodiments, each message between the backend system 108 and the user mobile device 102 may be saved to the user journey in the user journey database 112. In block 338, the client device 106 and therefore the user may be redirected to a completion or "thank you" web page or web resource.

Although the blocks 302-338 are described in a relatively serial manner, it should be appreciated that various blocks of the method 300 may be performed in parallel and/or another order in some embodiments.

Figure 5:
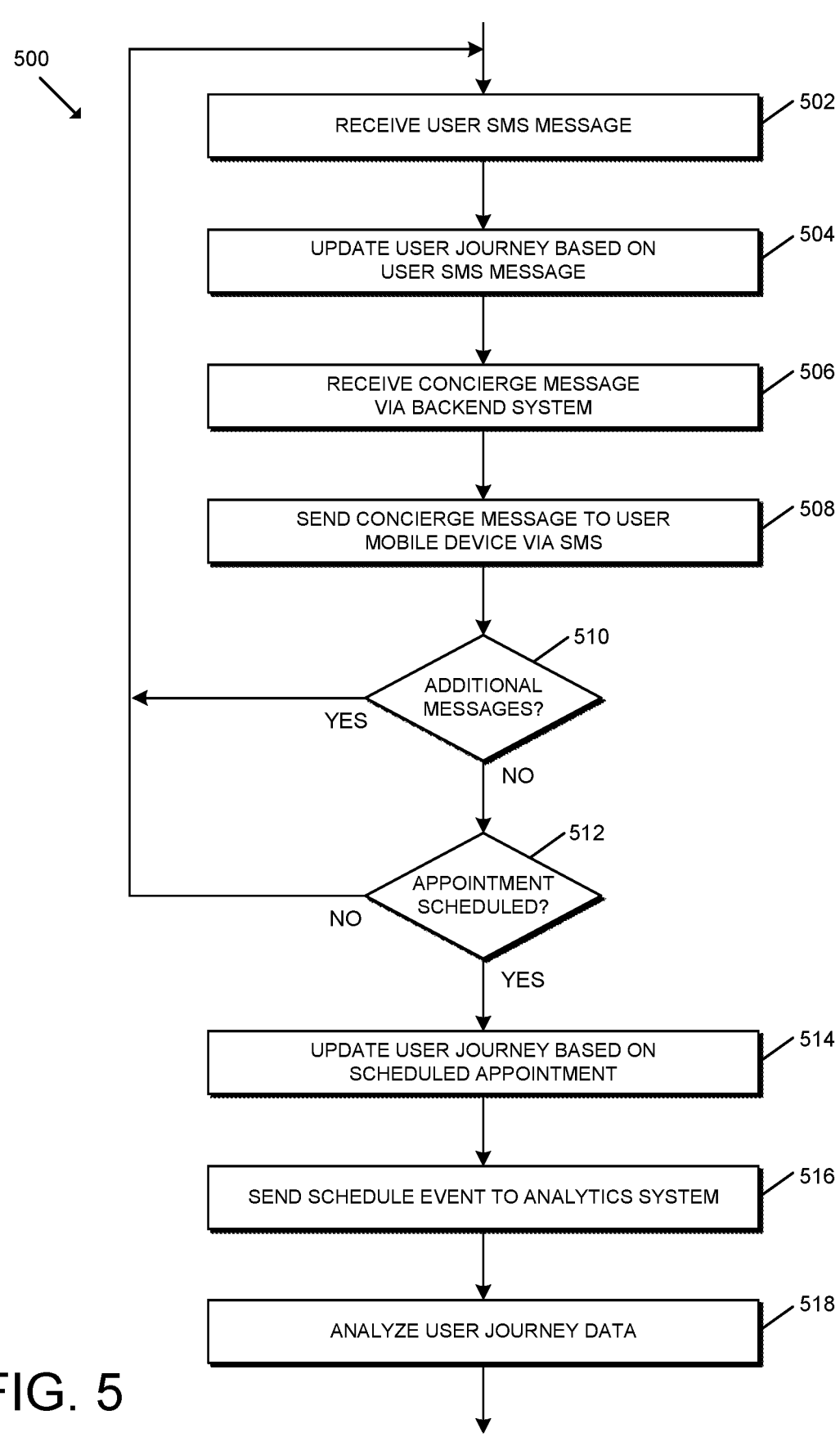
FIG. 5 is a simplified flow diagram of at least one embodiment of a method for leveraging a multi-modal digital communication architecture for patient engagement.

Referring now to FIG. 5, in use, the system 100 may execute a method 500 for leveraging a multi-modal digital communication architecture for patient engagement. It should be appreciated that the particular blocks of the method 500 are illustrated by way of example, and such blocks may be combined or divided, added or removed, and/or reordered in whole or in part depending on the particular embodiment, unless stated to the contrary.

The illustrative method 500 begins with block 502 in which the backend system 108 receives a user's SMS message sent by the user via the user mobile device 102 (e.g., by the user replying to the SMS message from the backend system 108 described above in reference to the method 300 of FIGS. 3-4). In some embodiments, the user's SMS message is received by an SMS service of the backend system 108, which may broadcast the SMS message to a notification service that provides the user's SMS message to the medical concierge via a user interface of the backend system 108. Additionally, as described above, it should be appreciated that each of the messages between a user and the backend system 108 may be stored to the user's journey in the user journey database 112, and such messages are accessible to the analytics system 110 for analysis.

In block 506, the backend system 108 receives a medical concierge's message to the user (e.g., replying to the user's SMS-generated message). It should be appreciated that the medical concierge may view user messages and reply to those messages via a user interface of the backend system 108. The backend system 108 may forward the concierge message to the notification service, which may then generate and transmit an SMS-based message to the user mobile device 102 in block 508. Additionally, as described above, the user journey database 112 may be updated accordingly. It should be appreciated that the user and the medical concierge may exchange multiple messages with one another in an effort to schedule an initial appointment with a healthcare provider in relation to the user's/patient's potential surgical needs. Accordingly, in block 510, if there are additional messages to be exchanged, the method 500 returns to block 502. However, if there are no further messages to be exchanged, the method 500 advances to block 512 in which the backend system 108 determines whether an appointment is to be scheduled. If not, the method 500 may return to block 502 or terminate depending on the particular circumstances. However, if an appointment is to be scheduled, the method 500 advances to block 514 in which the backend system 108 updates the user journey in the user journey database 112 based on the scheduled appointment (e.g., the agreed upon date, provider name, etc.). As described above, it should be appreciated that an automated concierge may communicate with the user in some embodiments (e.g., exclusively or in conjunction with a human concierge). It should be further appreciated that, in some embodiments, machine learning and/or other artificial intelligence technologies may be leveraged to facilitate the automated scheduling of appointments or other events.

In block 516, the backend system 108 may send a schedule event to the analytics system 110 indicating that an appointment has been scheduled, along with the associated information. In block 518, the backend system 108 or, more specifically, the analytics system 110 may analyze the user journey data and/or other patient-related data. In doing so, it should be appreciated that the analytics system 110 may leverage machine learning, computer vision, and/or other analytical technologies as described above. For example, in some embodiments, the analytics system 110 may analyze the user journey using machine learning to prequalify the user for a particular procedure based on patient data of the user (e.g., patient visit data, meta data, patient insurance information, etc.), insurance criteria (e.g., insurance requirements associated with various diagnostic codes, temporal conditions, etc.), patient and/or other image analysis (e.g., using computer vision and/or other artificial intelligence technologies), diagnostic lab data for the user, electronic health records (EHR) provider note information (e.g., the physician-supplied medical note), third party data (e.g., pharmacy information, etc.), claims data (e.g., how many antibiotics a patient has been on), sensor data (e.g., from wearable health-monitoring and/or environment-monitoring devices), and/or other relevant data. Accordingly, based on such analysis, it should be appreciated that by the time a healthcare provider is contacted for a surgical consultation, the backend system 108 may have already analyzed the substantive conversation between the user/patient and the medical concierge, and pre-qualified and pre-screened the patient to be ready for a procedure (e.g., a surgical procedure) that will likely satisfy insurance-mandated criteria. In other words, the backend system 108 leverages predictive analytics to determine the likelihood that the user/patient will ultimately schedule a surgical or other procedure using machine learning based on the various accessible data.

It should be appreciated that, in some embodiments, the backend system 108 may generate one or more refined notes based on the machine learning-based analysis of the user journey and related data as described herein. In other words, the backend system 108 may also generate a refined note that is more likely to satisfy insurance-mandated criteria, AI-based scoring, and/or other conditions than a traditional EHR-provided note.

Although the blocks 502-518 are described in a relatively serial manner, it should be appreciated that various blocks of the method 500 may be performed in parallel and/or another order in some embodiments.

By integrating the technologies described herein with an EHR or receiving feedback information, the backend system 108 may also track the surgeries being performed and analyze the patterns associated with those surgeries. For example, the backend system 108 may leverage machine learning to analyze the user journeys that ultimately resulted in a particular surgery to update the machine learning models, identify and address any outlier data, and improve health outcomes for future patients. Further, by identifying the user journey patterns associated with a particular health condition or procedure, the backend system 108 may also proactively identify patient behavior or patterns and notify patients of various health risks far in advance of typical presentation times. For example, the technologies described herein may be leveraged for the early prediction of serious illnesses such as cancers, multiple sclerosis, and other conditions.

The technologies described herein may also be leveraged to track patient flow better than the typical reliance on historical claims data. For example, the backend system 108 may provide real-time data on patients such as what the patients are saying to medical professionals and concierges, the quality of the patient, and the correlation/probability of a particular ICD-10 diagnosis. In some embodiments, the backend system 108 may function to integrate post-operation communication with pharmacy data to remind patients to take their post-operation medications and have the patient verify that the medication was taken. Further, if post-operation patients have follow-up questions, the patient may be seamlessly connected to the healthcare provider via the established SMS communication channel with the backend system 108 to the medical concierge.

What is claimed is:

1. A method of leveraging a multi-modal digital communication architecture for patient engagement, the method comprising:

generating, by a computing system, a session identifier for a session between the computing system and a client device of a user in response to loading a web resource on the client device;

creating, by the computing system, a user journey in a database of the computing system;

associating, by the computing system, the session identifier with the user journey;

validating, by the computing system, user registration information of the user, wherein the user registration information includes a name of the user and a mobile number of a user mobile device of the user;

receiving, by the computing system, a user message from the user via the client device;

sending, by the computing system, a Short Message Service (SMS) message to the user mobile device in response to receiving the user message from the user via the client device to establish an SMS-based communication channel with the user; and analyzing, by the computing system, the user journey using machine learning to prequalify the user for a particular medical procedure, based on data indicative of insurance criteria associated with one or more of a diagnostic code or a temporal condition, wherein analyzing further includes utilizing predictive analytics to analyze a substantive conversation that is represented in the user journey and that includes communications transmitted via the SMS-based communication channel between the user and a concierge associated with the computing system, determining, based on the predictive analytics, a probability that the user will schedule the medical procedure, and performing, in response to determining the probability that the user will schedule the medical procedure, prequalification operations for prequalifying the user for the medical procedure to ensure that the patient will satisfy the insurance criteria.

2. The method of claim 1, wherein the user mobile device comprises the client device.

3. The method of claim 1, further comprising associating the user journey with the user registration information.

4. The method of claim 1, further comprising storing the user message and the SMS message to the database in association with the user journey.

5. The method of claim 1, wherein validating the user registration information of the user comprises:

transmitting, by the computing system, a random code to the user mobile device via SMS; and receiving, by the computing system, a user entry of the random code via the client device.

6. The method of claim 1, wherein analyzing the user journey comprises analyzing one or more images of the user using computer vision.

7. The method of claim 1, wherein analyzing the user journey comprises analyzing the user journey using machine learning based on patient data of the user and the insurance criteria.

8. The method of claim 1, wherein analyzing the user journey comprises analyzing at least one of diagnostic lab data for the user or electronic health record provider note information associated with a user visit.

9. The method of claim 1, further comprising generating a refined note based on the analysis of the user journey using machine learning to prequalify the user for the particular procedure.

10. The method of claim 1, further comprising:

identifying, by the computing system, a pattern in reference user journey data of a set of other users;

determining, by the computing system, an association between the identified pattern and a defined health condition;

determining, by the computing system and based on the identified pattern and the user journey data, whether the defined health condition applies to the user; and notifying, by the computing system and in response to a determination that the defined health condition applies to the user, the user of the defined health condition.

11. A computing system for leveraging a multi-modal digital communication architecture for patient engagement, the computing system comprising:

at least one processor; and at least one memory comprising a plurality of instructions stored thereon that, in response to execution by the at least one processor, causes the computing system to:

generate a session identifier for a session between the computing system and a client device of a user in response to loading a web resource on the client device;

create a user journey in a database of the computing system;

associate the session identifier with the user journey;

validate user registration information of the user, wherein the user registration information includes a name of the user and a mobile number of a user mobile device of the user;

receive a user message from the user via the client device;

send a Short Message Service (SMS) message to the user mobile device in response to receipt of the user message from the user via the client device to establish an SMS-based communication channel with the user; and analyze the user journey with machine learning to prequalify the user for a particular medical procedure, based on data indicative of insurance criteria associated with one or more of a diagnostic code or a temporal condition, wherein to analyze the user journey includes to utilize predictive analytics to analyze a substantive conversation that is represented in the user journey and that includes communications transmitted via the SMS-based communication channel between the user and a concierge associated with the computing system, determine, based on the predictive analytics, a probability that the user will schedule the medical procedure, and perform, in response to the determination of the probability that the user will schedule the medical procedure, prequalification operations for prequalifying the user for the medical procedure to ensure that the patient will satisfy the insurance criteria.

12. The computing system of claim 11, wherein the user mobile device comprises the client device.

13. The computing system of claim 11, wherein the plurality of instructions further causes the computing system to associate the user journey with the user registration information.

14. The computing system of claim 11, wherein the plurality of instructions further causes the computing system to store the user message and the SMS message to the database in association with the user journey.

15. The computing system of claim 11, wherein to validate the user registration information of the user comprises to:

transmit a random code to the user mobile device via SMS; and receive a user entry of the random code via the client device.

16. The computing system of claim 11, wherein to analyze the user journey comprises to analyze one or more images of the user using computer vision.

17. The computing system of claim 11, wherein to analyze the user journey comprises to analyze the user journey using machine learning based on patient data of the user and the insurance criteria.

18. The computing system of claim 11, wherein to analyze the user journey comprises to analyze at least one of diagnostic lab data for the user or electronic health record provider note information associated with a user visit.

19. The computing system of claim 11, wherein the plurality of instructions further causes the computing system to generate a refined note based on the analysis of the user journey using machine learning to prequalify the user for the particular procedure.

20. The computing system of claim 11, wherein the plurality of instructions further cause the computing system to:

identify a pattern in reference user journey data of a set of other users;

determine an association between the identified pattern and a defined health condition;

determine, based on the identified pattern and the user journey data, whether the defined health condition applies to the user; and notify, in response to a determination that the defined health condition applies to the user, the user of the defined health condition.

* * * * *